United States Patent
Leiter et al.

(10) Patent No.: US 8,433,415 B2
(45) Date of Patent: *Apr. 30, 2013

(54) APPARATUS AND METHOD FOR MODULATING NEUROCHEMICAL LEVELS IN THE BRAIN

(75) Inventors: James C. Leiter, Woodstock, VT (US); Mykyta M. Chernov, Lebanon, NH (US); David W. Roberts, Lyme, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/449,559

(22) Filed: Apr. 18, 2012

(65) Prior Publication Data

US 2012/0209347 A1    Aug. 16, 2012

Related U.S. Application Data

(60) Division of application No. 12/649,963, filed on Dec. 30, 2009, which is a continuation-in-part of application No. 11/243,565, filed on Oct. 5, 2005, now abandoned.

(60) Provisional application No. 60/615,995, filed on Oct. 5, 204, provisional application No. 60/616,000, filed on Oct. 5, 2004, provisional application No. 60/669,743, filed on Apr. 8, 2005, provisional application No. 60/669, 483, filed on Apr. 8, 2005.

(51) Int. Cl.
    *A61N 1/36*    (2006.01)

(52) U.S. Cl.
    USPC ............. 607/45; 607/48; 600/544; 600/545

(58) Field of Classification Search ............ 600/544, 600/545; 607/45, 48
    See application file for complete search history.

(56) References Cited

U.S. PATENT DOCUMENTS

| | | |
|---|---|---|
| 3,850,161 A | 11/1974 | Liss |
| 5,683,422 A | 11/1997 | Rise |
| 5,792,186 A | 8/1998 | Rise |
| 5,978,702 A | 11/1999 | Ward et al. |
| 6,016,449 A | 1/2000 | Fischell et al. |
| 6,066,163 A | 5/2000 | John |
| 6,366,813 B1 | 4/2002 | DiLorenzo |
| 6,480,743 B1 | 11/2002 | Kirkpatrick et al. |
| 6,687,525 B2 | 2/2004 | Llinas et al. |
| 6,690,974 B2 | 2/2004 | Archer et al. |
| 6,810,285 B2 | 10/2004 | Pless et al. |
| 6,819,956 B2 | 11/2004 | DiLorenzo |
| 6,920,359 B2 | 7/2005 | Meadows et al. |
| 2002/0013612 A1 | 1/2002 | Whitehurst |
| 2003/0083716 A1 | 5/2003 | Nicolelis et al. |
| 2006/0058856 A1 | 3/2006 | Morrell |
| 2006/0195157 A1* | 8/2006 | Lee et al. .................... 607/46 |
| 2006/0241717 A1 | 10/2006 | Whitehurst et al. |

* cited by examiner

*Primary Examiner* — Rex R Holmes
(74) *Attorney, Agent, or Firm* — Lathrop & Gage LLP

(57) ABSTRACT

A treatment for Parkinson's Disease uses a stimulus electrode implanted in a subthalamic nucleus with a chemosensor implanted in a globus pallidus pars interna (GPi) of the subject. A level of a neurochemical is sensed with the chemosensor, and compared to a desired level. When the level of the neurochemical is less than desired, an electrical stimulation is provided to the stimulus electrode. In alternative embodiments, the neurochemical sensed is glutamate or dopamine. An alternative system uses a chemosensor implanted in the striatum instead of the GPi. An alternative system for treating benign essential tremor uses a stimulus electrode implanted in the thalamus with feedback taken from a chemosensor in the striatum.

6 Claims, 6 Drawing Sheets

APPARATUS AND METHOD FOR MODULATING NEUROCHEMICAL LEVELS IN THE BRAIN

RELATED APPLICATIONS

This application is a divisional application of U.S. patent application Ser. No. 12/649,963, filed Dec. 30, 2009, which is a continuation-in-part of U.S. patent application Ser. No. 11/243,565 filed Oct. 5, 2005, now abandoned which claims priority to U.S. Provisional Application Ser. No. 60/615,995 filed Oct. 5, 2004; U.S. Provisional Application Ser. No. 60/616,000 filed Oct. 5, 2004; U.S. Provisional Application Ser. No. 60/669,743 filed Apr. 8, 2005; and U.S. Provisional Application Ser. No. 60/669,483 filed Apr. 8, 2005, the disclosures of which are incorporated herein by reference.

BACKGROUND

Regulation of levels of various neurochemicals and other chemicals in the central and peripheral nervous system is likely to provide a critical mechanism for the treatment and/or prevention of neurodegenerative and psychiatric diseases in humans.

For purposes of this document, Neurochemical refers to a chemical substance released from or which acts on neurons and/or glia during, or as a result of, neurotransmission or neurosecretion. Neurochemicals include, but are not limited to neurotransmitters, neuromodulators, neuropeptides, and/or neuroregulators. Exemplary known neurochemicals include dopamine, acetylcholine, glutamate, norepinephrine, epinephrine, serotonin, and their precursors and metabolites (e.g., L-DOPA and DOPAC, respectively). The central nervous system may include, but is not limited to, structures in the brain (including the spinal cord) such as the thalamus, substantia nigra pars compacta and pars reticulata, cerebral cortex, caudate-putamen, globus pallidus, cerebellum, limbic structures, cranial nerve nuclei, and brain stem. The peripheral nervous system refers to peripheral ganglia of the somatic and/or autonomic nervous system, such as, but not limited to, spinal ganglia, enteric ganglia, and cardiac ganglia. The peripheral nervous system, as used herein, also refers to the target organs of the peripheral autonomic nervous system, including, but not limited to, the adrenal gland, carotid body, and smooth muscle.

Concentrations of neurochemicals are altered in many disease states, including psychiatric disorders and some neurodegenerative diseases, including some movement disorders such as Parkinson's Disease (PD). Many medications used to treat these disorders affect neurochemical levels within the central nervous system, and it is believed that their effectiveness is a consequence of their effect on those neurochemical levels. For example, both Tricyclic Antidepressants and Selective Serotonin Reuptake Inhibitors (SSRI's) have an effect of increasing serotonin levels and are commonly used to treat depression, among other conditions. Similarly drugs that affect dopamine levels, including the dopamine-precursor drug L-DOPA, are commonly used to treat PD, among other conditions. Even amphetamine has an effect on neurochemical concentrations; its effect on wakefulness is believed to be due to its effect on norepinephrine, serotonin, and dopamine levels in the brain.

Patients suffering from tremor and other symptoms of PD, and similar conditions, may undergo surgery to lesion a part of the brain (e.g., the ventral intermediate (Vim) nucleus of the thalamus the internal segment of the globus pallidus (GPi) (FIG. 1), or the subthalamic nucleus (STN)), which in some cases may afford some relief. Such a lesion is, however, irreversible, placement and size of the lesion can be difficult to control precisely, and such lesions may in some cases lead to permanent side effects. It is desirable to be able to produce relief in a reversible manner such that possible disability due to such permanent side effects may be avoided.

It has been proposed that some of these conditions can be treated by applying drugs or electrical stimulation directly into areas of the brain that are involved in these conditions. For example, Whitehurst, US 2007/0100393, paragraph 36, refers to "infusion of one or more drugs at the stimulation site and/or applying one or more electrical current pulses to the stimulation site." The one or more stimulation sites referred to in Whitehurst "may include . . . the [nucleus of the solitary tract] NTS, the ventral intermediate thalamic nucleus, the GPi, the [external segment of the globus pallidus] GPe, the STN, the pallido-subthalamic tracts, the substantia nigra pars reticulare, the pallido-thalamic axons, the putamen (Put) to GPe fibers, the subthalamopallidal fibers, the putamen to GPi fibers, the cerebellum, and/or any other suitable location within the brain." Whitehurst, however, fails to describe treatment of a motor disorder through using a neurochemical-sensitive chemosensor to provide feedback control of stimulation of another part of the brain.

It is known in the art that electrical stimulation of deep brain structures is capable of treating the symptoms of some diseases, such as Parkinson's Disease (see, e.g., Benabid et al, 2000 Neurology, 55:s40-44, see also, Obeso et al, Deep-Brain Stimulation Of The Subthalamic Nucleus Or The Pars Interna Of The Globus Pallidus In Parkinson's Disease, N Engl J Med, Vol. 345, No. 13, Sep. 27, 2001, 957-963).

Precise electrode placement in small, deep, neurological structures like the STN can be difficult to achieve. Further, subjects often have differing degrees of disease; subjects may often have different degrees of disease between left and right structures in the same brain. In consequence, open-loop deep-brain stimulation devices are difficult to adjust for optimum effectiveness.

While devices having the ability to measure release of neurochemicals as evoked by electrostimulation in particular brain regions are known (see, e.g., Dugast et al., 1994 Neuroscience 62:647), the known art fails to teach a method or device that utilizes such information to initiate or automatically adjust electrical deep brain stimulation (DBS) treatment of PD in an individual using a chemosensor in one part of the brain to control stimulation in another part of the brain to treat a specific disorder.

Whitehurst, US 2007/0100393 A1, discusses treatment of movement disorders through a device implanted or partially-implanted in a subject that provides brain stimulation, paragraph 74, and suggests generally that it may be appropriate to monitor pH, muscle electromyographic data, head or limb accelerations, or to use electroencephalographic data to provide control information for a brain stimulator.

Implantable, open-loop, stimulators intended for long-term use are known in the art. For example, the Medtronic® Activa RC 37612 provides for stimulation on one or two leads with through-skin programmability. Medtronic is a trademark of Medtronic, Inc., Minneapolis, Minn. The Activa RC 37612 provides for pulse widths of 60 to 450 microseconds and pulse rates of 2 to 250 Hz, with pulse voltage in voltage mode programmable from 0 to 10.5 volts in 0.05 volt steps or current in current mode programmable from 0 to 25.5 milliamps in 0.1 milliamp steps. Typical available neurostimulators do not have automatic feedback control and require extensive testing and calibration. These commercially available neurostimulators are provided with stimulus lead, or electrode, assemblies typically having four electrodes near their tips, and the stimulator may be programmed to use different combinations of the electrodes.

SUMMARY

A principle feature of the present invention is to provide electrical stimulation applied to the central and/or peripheral nervous system of an individual using a deep brain stimulator (DBS) in response to the detection of a change in neurochemical levels in a particular region of the central/peripheral nervous system.

The treatment method features a deep-brain-stimulator (DBS) device that includes a neurochemical sensor at a first location of the central nervous system, a control module having electronic circuitry capable of determining whether an amount of neurochemical is different from a predetermined target amount, and a stimulation module under control of the control module. The sensor is used to measure the amount of a particular neurochemical in the region of the first location of the central nervous system, and that information is relayed to the control module. The sensor may also be adapted to measure the levels of neurochemicals induced at the first location by electrical stimulation to the central nervous system at a second location of the central nervous system. The sensor may be any sensor that permits the measurement of neurochemicals in vivo, including, but not limited to, sensors that may be used in microdialysis, constant potential amperometry, fast-scan cyclic voltammetry, high-speed chronoamperometry, differential normal-pulse voltammetry, or any number of electroanalytical techniques known in the art. If the amount of neurochemical measured by the sensor is significantly different from a desired amount, a signal indicative thereof is sent to the stimulation module. The stimulation module then generates an electrical signal that is transmitted to the second location in the central nervous system of the individual.

DETAILED DESCRIPTION OF THE EMBODIMENTS

Figure 1:
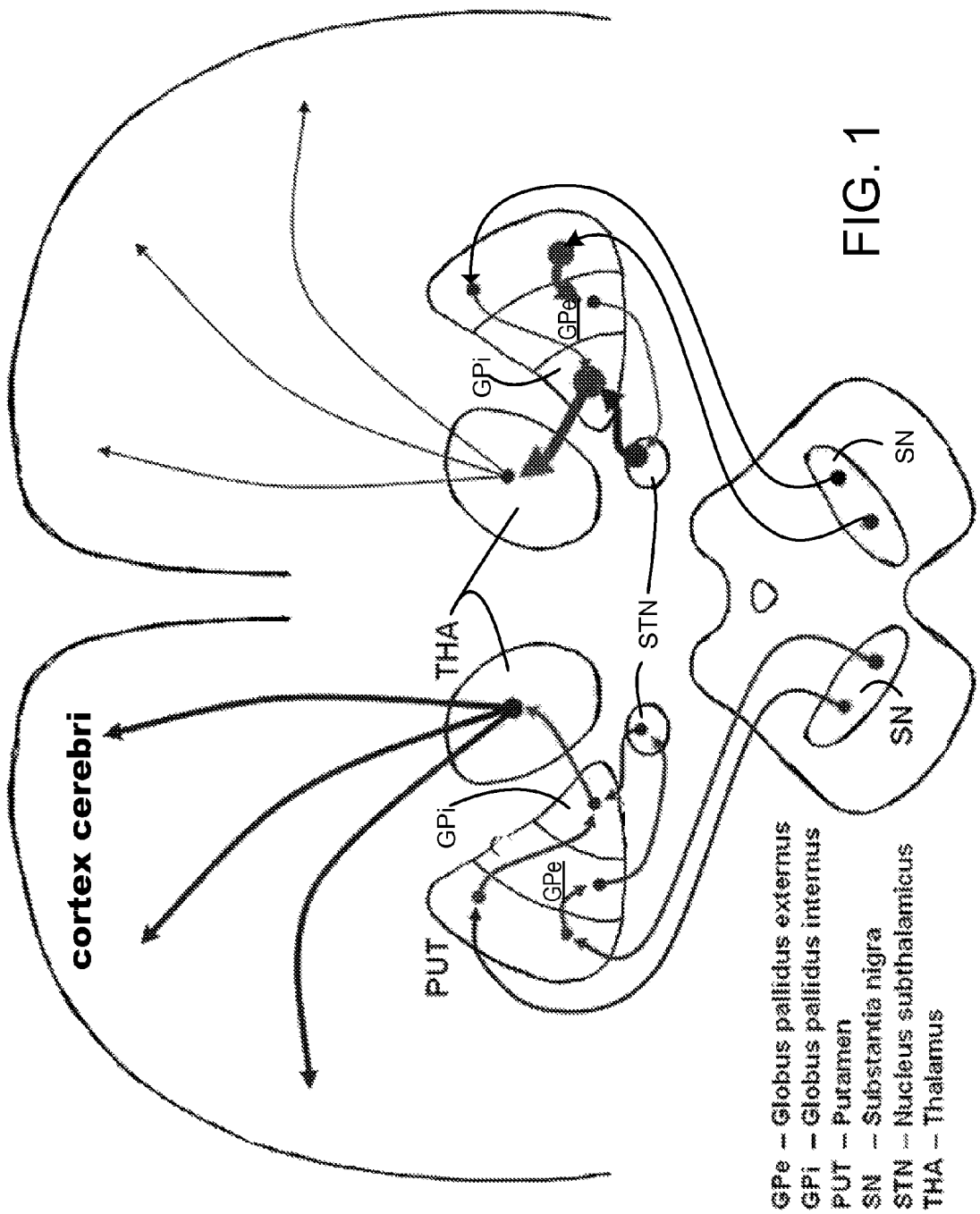
FIG. 1 is a schematic diagram of brain showing pathways involving the GPi and STN that are believed active in Parkinson's Disease.
Figure 2:
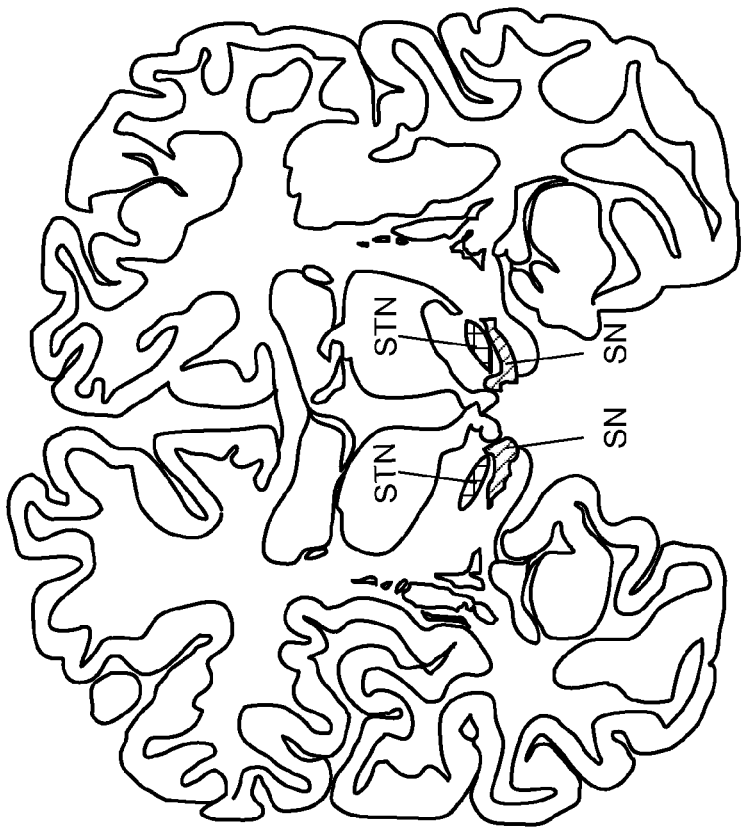
FIG. 2 is a sketch of relevant features of a section of brain showing the subthalamic nucleus (STN).
Figure 3:
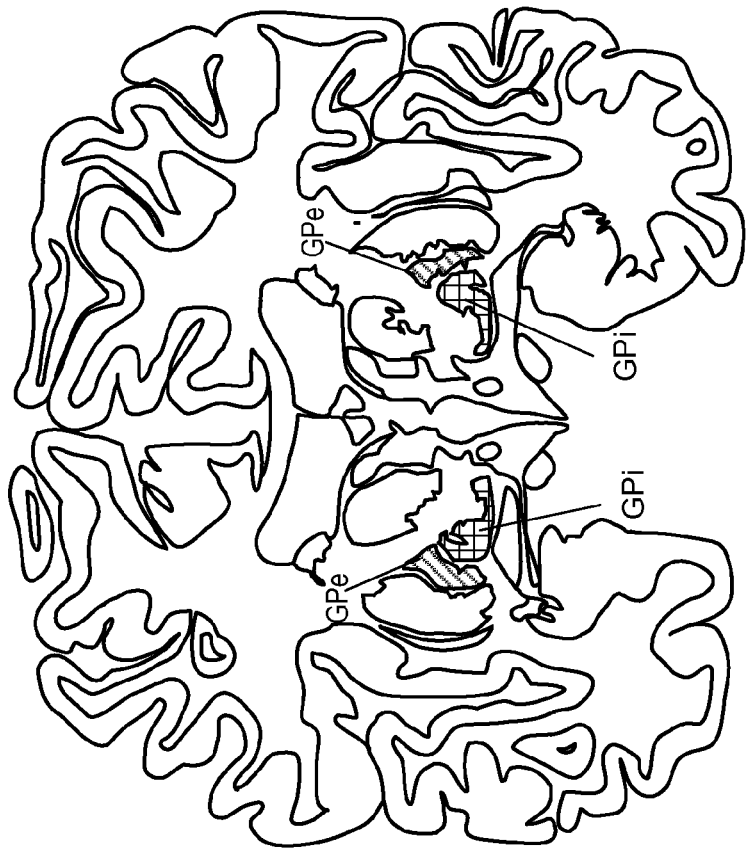
FIG. 3 is a sketch of relevant features of a section of brain showing the globus pallidus (GPi and GPe).

Pathways believed to be involved in Parkinson's Disease are illustrated schematically in FIG. 1. Key portions of the brain involved in these pathways are also illustrated in the sketches of sectioned brain in FIGS. 2 and 3. The Substantia Nigra (SN) is connected through Putamen (Put) and the Globus Pallidus Pars Externa (GPe) to the Globus Pallidus Pars Interna (GPi). Some pathways from the SN to the GPi pass through the Subthalamic Nucleus (STN). It is known that Parkinson's Disease involves degradation of dopaminergic neurons of the SN, and many prior treatments, including use of the drug L-DOPA, have involved medications active on dopaminergic neurons in the SN.

Rat Studies of Neurotransmitter Level Response in STN to Stimulus of STN

The present inventors have previously studied the possibility of feedback control of a neurotransmitter level in the STN of rats using a glutamate-sensitive chemosensor located in the STN that measures the neurotransmitter level and conveys these measurements to a feedback stimulus controller. The feedback stimulus controller then provided stimulus pulses to an electrical stimulus probe located in the STN. This work was published in Behrend et al, Toward Feedback Controlled Deep Brain Stimulation: Dynamics Of Glutamate Release In The Subthalamic Nucleus In Rats, Journal of Neuroscience Methods 180 (2009) 278-289, the contents of which are included herein by reference.

A glutamate-sensitive biosensor was obtained. The glutamate-sensitive biosensor used herein measures a glutamate concentration using glutamate oxidase to catalyze the formation of hydrogen peroxide and alpha-ketoglutaric acid from extracellular glutamate and oxygen. The oxidation of the hydrogen peroxide formed is detected by a platinum-iridium (Pt—Ir) electrode held at a potential of 600 mV. The 90% response time of the biosensor for glutamate detection is between one and four seconds according to the manufacturer. The data from the biosensor was analyzed and transmitted to a computer and sampled at a rate of once per second. Glutamate calibration curves were generated in vitro for each biosensor before each experiment by increasing the concentration of glutamate incrementally from 0 to 3 millimolar in phosphate-buffered saline (PBS) (at pH 7.4) according to the manufacturer's instructions. Sensitivity to ascorbate, an interfering substance, was tested using increments of 250 micromolar ascorbate, and any biosensor with a response to 250 micromolar ascorbate greater than 0.5 nanoamp was discarded. Experiments with the sensor in vitro showed a response to rising glutamate levels having a time constant of 0.85 seconds and a falling time constant of about 2.66 seconds.

High frequency stimulation (HFS) for purposes of this document includes electrical stimulation of brain tissue with electrical pulses having current typically between fifty and four hundred microamperes, with voltages in the range from minus one-half to minus five volts. Such HFS typically involves pulses at a rate of between one hundred and one hundred eighty pulses per second, with a pulse length of between ten and one hundred microseconds.

During the experiments using both glutamate chemosensor and stimulus probes in the STN of anesthetized rats, the glutamate levels were measured once per second, and adjustments to setting of a stimulus generator were made in response to the glutamate levels. An alternative HFS embodiment found effective in the rats used stimulation pulse widths of between 6.6 and 10 milliseconds having a duty cycle of ten percent with pulse repetition frequencies of both 100 and 150 Hertz, using sufficient current that each stimulus pulse injected charge of 13 microcoulombs per square centimeter of stimulus electrode area. The results were used to derive a transfer function relating stimulus to glutamate levels in the STN. The transfer function was of a form of an exponential equation as a function of time:

$$\text{rising phase} \rightarrow \text{glutamate} = c(1-e^{-t/\tau}) \quad \text{Eqn. 1:}$$

$$\text{falling phase} \rightarrow \text{glutamate} = c(e^{-t/\tau 2}) \quad \text{Eqn. 2:}$$

where 'c' represents the maximum glutamate value reached after prolonged stimulation, 'τ' is the rising time constant of the response, and 't' is time; where 'c' represents the minimum glutamate value reached after stimulation ceased, 'τ2' is a falling time constant of the response, and 't' is time.

In the rat, the τ for 'on' response of glutamate for 100 Hertz pulse rate stimulation was 448 seconds, or for 150 Hertz stimulation τ was 277 seconds. The time constant τ2 for the 'off' response was 1989 seconds at a pulse rate of 100 Hertz and 940 seconds at a pulse rate of 150 Hertz.

In addition to the foregoing assessment of the model fit, we also modified the conditions of stimulation to determine whether the model developed using one pattern of stimulation could accurately predict glutamate responses to differing patterns of HFS in the STN. Therefore, we generated two new stimulation sequences. In the first of these, we used a different pseudorandom binary sequence (PRBS) and assessed the relationship between extracellular glutamate levels and this new PRBS of HFS and the predicted response using the transfer function derived from the original PRBS. In the second stimulation sequence, we shortened the PRBS element length to 25 seconds, used another new PRBS and determined whether the extracellular glutamate response to this pattern of stimulation could be predicted from the transfer function derived from the original PRBS.

Figure 5:
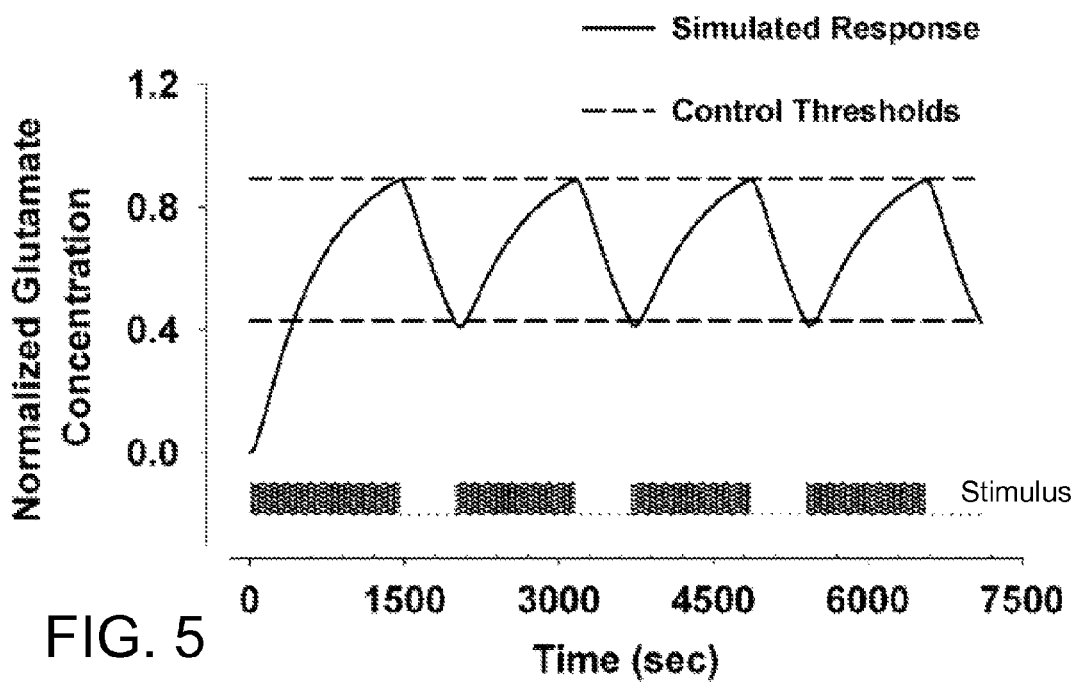
FIG. 5 is an illustration of a simulation of feedback control of glutamate levels using both a chemosensor and a stimulus electrode in the STN.
Figure 6:
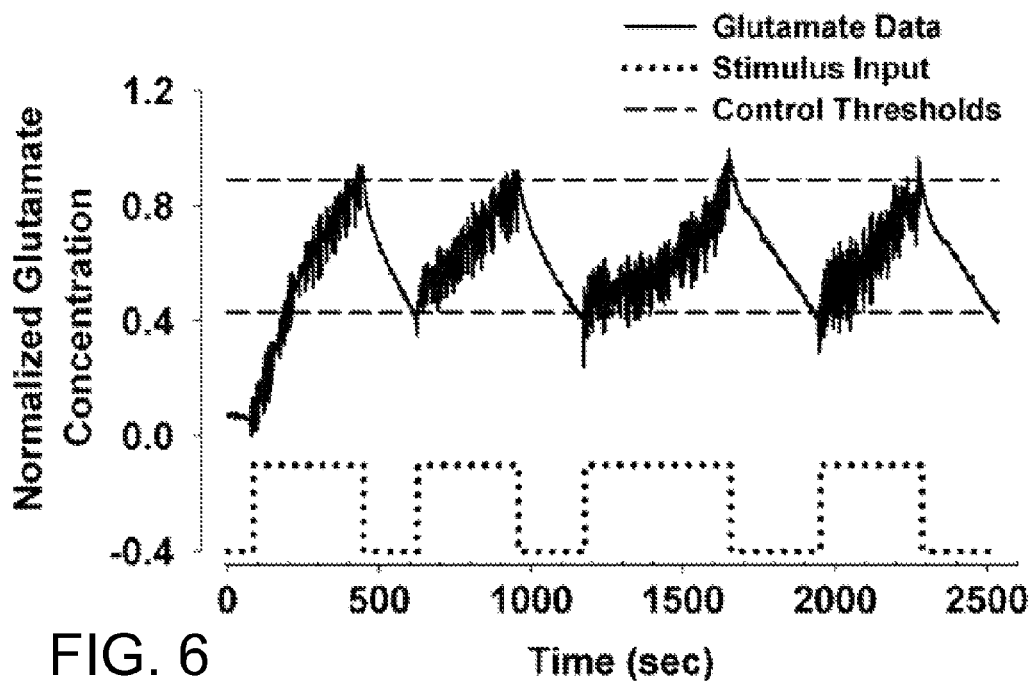
FIG. 6 is an illustration of feedback control of glutamate levels using both a chemosensor and a stimulus electrode in the STN in live rats.

We used the transfer function that we developed to simulate computationally a variety of stimulation protocols and determine which pattern of HFS most effectively controlled extracellular glutamate levels within the STN at any target value that we selected. This simulated response is illustrated in FIG. 5. We tested the feasibility of feedback control of DBS in anesthetized animals by using the HFS sequence developed from the transfer function and computer simulation studies to determine whether this HFS sequence actually provided real time control of extracellular glutamate levels. Experimental results of feedback control of glutamate levels within the STN are illustrated in FIG. 6.

Adjustment of the HFS sequences using STN glutamate levels for feedback control of the stimulus patterns to the STN does indeed seem to control extracellular glutamate within the STN.

In a particular alternative embodiment, the stimulus frequency ranges between 150 Hertz and 180 Hertz. In this embodiment, the pulse width remains constant at a predetermined level preferably between ten and one hundred microseconds, and the stimulus pulse pattern is adjusted by a computer algorithm to maintain extracellular glutamate levels at a predetermined target level in a range of target levels from approximately ten to two hundred micromolar. The pulse pattern has sequences of bursts of pulses where each burst has a pulse count that is adjusted by the controller to provide more pulses when glutamate levels are low, and fewer or no pulses when the glutamate levels are high. It was found that this embodiment was able to maintain a predetermined level of glutamate in the STN of the rat using feedback control derived from measurements of glutamate levels in the rat's STN.

In an alternative embodiment, instead of, or in addition to, providing bursts of pulses with a modulated pulse count, stimulus intensity is adjusted by the following mechanisms: (i) the intensity of each pulse may be adjusted by changing the current or voltage of each stimulus, as appropriate for the stimulator used, and/or (ii) coupling of the pulses to the brain tissue may be adjusted by switching pulse delivery between more effective and less effective electrode pairs in an electrode assembly. In addition, the duration of a sequence of pulses may be lengthened or shortened to change the average level of stimulation over time. In an embodiment, we envision changing both the stimulus intensity of each pulse and also the pattern of pulse sequences to optimize the level of the selected target neurotransmitter.

Stimulating the STN, Feedback From Chemosensor in Globus Pallidus Pars Interna

Experiments in rats subjected to toxins such as 6-hydroxydopamine (6-OHDA) that selectively block or destroy dopaminergic neurons showed that loss of dopaminergic neurons in the SN did not substantially alter the transfer function of stimulus in the STN to glutamate levels in the STN. Loss of dopaminergic neurons in the SN occurs during Parkinson's Disease.

It was found by experiment in these rats that the transfer function from stimulus in the STN to glutamate levels in the globus pallidus pars interna (GPi) is significantly altered by loss of dopaminergic neurons in the SN due to 6-OHDA exposure. It is believed that loss of dopaminergic neurons due to 6-OHDA exposure is an experimental model in rats that provides results applicable to human PD.

It is expected that feedback control of an electrostimulation treatment intended to restore neurochemical levels to normal in affected parts of the human brain suffering from PD requires monitoring neurochemical levels in brain tissue along a path having a transfer function from the point of stimulus to the chemosensor that is substantially altered by loss of dopaminergic neurons in the SN.

Stimulator for Treatment of Parkinson's Disease With Feedback From GPi

In the proposed treatment (FIG. 7) for PD in humans by electrostimulation of the STN, it is considered desirable to control the stimulation by feedback from monitoring glutamate levels in the GPi. In an alternative embodiment, feedback control of electrostimulation in the STN is controlled by monitoring dopamine levels in the GPi.

Figure 4:
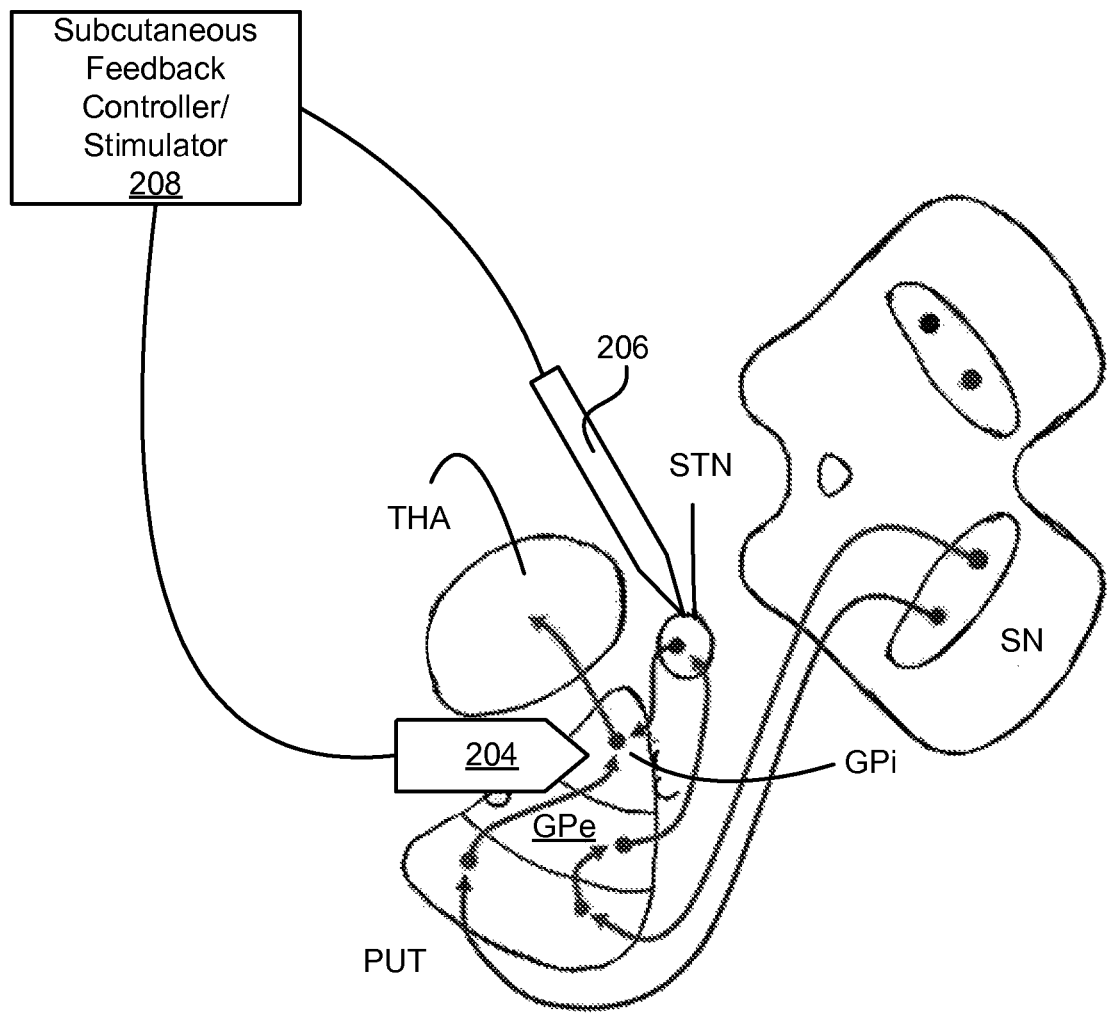
FIG. 4 is a not-to-scale illustration showing chemosensor placement in the GPi and electrode placement in the STN on a schematic diagram of brain for treatment of Parkinson's Disease.

In the treatment, an opening is created in the subject's skull to permit a surgeon to access the brain to implant the stimulation electrodes and chemosensor, and to bring wires from the electrodes and sensor to a controller placed subcutaneously. In an embodiment, the opening may be a burr hole. The surgeon implants 106 the chemosensor 204 with its sensor element in the GPi as illustrated in FIG. 4. The surgeon also implants 108 a stimulus electrode 206 such that its exposed electrode surface or surfaces are in or directly adjacent to the STN of the subject. The stimulus electrode 206 may be a stimulus electrode assembly having multiple electrodes near its tip, with each electrode having a separate conductor through the assembly to a control unit 208, and may be a commercially available stimulus lead assembly. Placement of stimulus electrode 206 may be performed using a stereotactic frame as known in the art of neurosurgery, and may be confirmed by one or both of monitoring of electrical activity in the brain through electrodes of the lead assembly, and trial stimulation through the lead assembly. Measurement of a transfer function between stimulaor electrode 206 in the STN and chemosensor 204 in the GPi may be performed during surgery, this transfer function is compared to an expected transfer function to confirm correct placement of both electrode and chemosensor. If stimulus through stimulus electrode 206 fails to produce an adequate neurochemical response at chemosensor 204 during implantation surgery, the electrode may be repositioned for better effectiveness.

In an embodiment for use in subjects having symptoms only on one side, electrode 206 and sensor 204 are implanted on only the affected side of the subject's brain. In an alternative embodiment for use in subjects having symptoms on both sides of their bodies, an electrode 206 is implanted in each STN and a sensor 204 is implanted in each GPi such that a pair are implanted on each side the subject's brain. For simplicity, only one pair is illustrated in FIG. 4.

The surgeon passes wires connected to each chemosensor 204 and stimulus electrode 206 through an opening in the subject's skull and couples 110 the wires to a control unit 208. The surgical wounds are then allowed to heal 111. Control unit 208 may also be implanted in the subject, and the control unit may be calibrated for use with the particular subject and implanted electrodes by providing periods of trial stimulation while monitoring neurochemical levels as measured by chemosensor 204 and subject patient symptoms. Further, effectiveness of various electrode combinations in a multiple-electrode assembly may be determined by providing trial stimulation through these electrode combinations while monitoring neurochemical levels and patient symptoms.

Control unit 208 then executes a sequence where the control unit provides stimulus pulses 112 through electrode 206 into the STN for a period of time sufficient to keep the targeted neurotransmitter levels near a specified level, in an embodiment within ten percent of the target level. The specified target level will be in the range of from ten to two hundred micromolar and will be prescribed by a physician based on the severity of the disease, response of the patient to stimulation of the STN, and the other therapies each patient receives. In an embodiment, the specified target level may be programmed to follow a diurnal pattern coordinated with a patient's anticipated activities to provide good control when the subject is performing fine motor activities while allowing recovery of stimulated tissue when the subject is inactive.

Control unit 208 contains a battery and signal amplification and signal conditioning apparatus for interfacing with chemosensor 206, a real-time clock, and a low-power microcontroller processor or custom logic circuit for comparing neurochemical levels as measured by the chemosensor to target levels and for generating stimulus pulse sequences. Control unit 208 generally operates automatically, however it is programmable through a programming pulse sequence electromagnetically coupled through the subject's skin, thereby allowing changes to the target levels and diurnal target level patterns, as well as selected stimulus parameters such as voltage, current, pulse rate, and pulse width, and diurnal patterns of operation without further surgery. In an alternative embodiment, the subject may use a restricted programming device to adjust target levels within limits set by a physician, or to allow the patient to choose rest periods or periods when particularly good control of symptoms is desired.

Stimulation may be continuous or intermittent

In an embodiment using intermittent stimulation, the duration of each burst of the stimulation pulses is determined based in part on the rising and falling times for that neurochemical in that patient. The control unit then reads chemosensor 204 to sense 114 a neurochemical level, such as glutamate or dopamine levels, in the GPi. If the sensed neurochemical level is less than the predetermined desired target level 116, the control unit repeats stimulus pulses 112 through the electrode 206 implanted in the STN on the same side of the subject's brain as the chemosensor 204. If the sensed neurochemical level is greater than the predetermined desired level the control unit waits 118 and repeats sensing of the neurochemical level. Since the neurochemical level must drop below the threshold before stimulation is resumed, and the delay is shorter than the time constants of the neurochemical levels in tissue, the net effect is to control the neurochemical level in the GPi near the desired level. In an alternative embodiment, a rising and a falling threshold is used. In this embodiment, if the sensed neurochemical level is above a stop-stimulating level when sensed 114, stimulus is stopped. The control unit then waits 118 while repeatedly re-reading the neurochemical level until the neurochemical level declines to a lower, resume-stimulation level of a target neurotransmitter range before resuming stimulation. The result is an alternating pattern of pulse-on activity characterized by increasing neurochemical levels, and pulse-off activity characterized by decreasing neurochemical levels, with net effect of controlling the stimulation to maintain a nearly-constant glutamate level in the GPi.

In an alternative embodiment using a burst-length-modulated, continuous, stimulation pulse pattern, the pulse pattern provided by the controller has sequences of bursts of pulses where each burst has a pulse count that is adjusted by the controller to provide longer bursts having more pulses when neurochemical levels are low, and short bursts with fewer or no pulses when the neurochemical levels are high.

In an alternative embodiment using continuous stimulation, instead of, or in addition to, providing bursts of pulses with a modulated pulse count, stimulus intensity is adjusted by the following mechanisms: (i) the intensity of each pulse may be adjusted by changing the current or voltage of each stimulus pulse within a programmed range as appropriate for the stimulator used, and/or (ii) coupling of the pulses to the brain tissue may also be dynamically adjusted by switching pulse delivery between more effective and less effective electrode pairs in a multiple-electrode electrode assembly.

In a particular embodiment feedback from the chemosensor may be used to modulate both the stimulus intensity of each pulse and also the pattern of pulse sequences to optimize the level of the selected target neurotransmitter.

The control unit may also dynamically change between stimulus pulse patterns as the neurochemical level approaches the target level. For example, in an embodiment, when a subject awakens and activates the control unit, the chemosensor may measure neurochemical levels that are quite low. The control unit then selects and provides stimulus through a pair of electrodes of a multiple-electrode assembly, and selects stimulus voltages and currents, together with long bursts of pulses that provide rapid increases in the neurochemical levels. When the neurochemical level approaches the target level or passes the target level for the first time since control unit activation, the selected electrode pair, and stimulus voltage or current, are reduced to a maintenance level stimulus. The control unit then enters an alternating pattern of pulses-on and pulses-off stimulus activity of, or burst-length modulates, the maintenance level stimulus, to maintain the measured neurochemical levels at the target level.

In subjects having a pair of chemosensor and electrode implanted on each side of the subject's brain, the chemosensor and electrode on the left side of the subject's brain operate as a pair independently of the chemosensor and electrode implanted on the right side of the subject's brain.

When the control unit provides stimulation to the STN, in an embodiment it provides high frequency stimulation of pulses each lasting 10-100 microseconds at a rate of 150-180 Hertz, where each pulse provides a sufficient current flux per square centimeter of stimulus electrode area to achieve the targeted neurotransmitter level at the site where it is measured.

Stimulator for Treatment of Parkinson's Disease With Feedback From Striatum

In an alternative embodiment, the stimulus electrode is implanted in the STN as previously discussed, however the chemosensor is implanted in the striatum instead of in the GPi. In humans, the striatum includes the putamen and the caudate nucleus. In this embodiment, the chemosensor is a dopamine-sensitive chemosensor.

It is expected that a transfer function from stimulation in the STN to dopamine levels in the striatum will depend on numbers of surviving dopaminergic neurons in the SN, and that the tremor of PD may respond to enhanced dopamine levels in the striatum. It is thus also expected that the tremor of PD may be controlled by electrostimulation of the STN, with the stimulation controlled to maintain a targeted level of dopamine in the striatum. In this embodiment, the voltage and pulse characteristics of the stimulus are the same as those previously discussed above with reference to stimulation of the STN with stimulation controlled to maintain a targeted level of glutamate in the GPi. In this embodiment, a flowchart of the method is essentially illustrated in FIG. 8.

In the proposed treatment (FIG. 8) for PD by electrostimulation of the STN, an opening or openings are created 304 in the subject's skull to permit a surgeon to access the brain to implant the stimulation electrodes and chemosensor, and to bring wires from the electrodes and sensor to a controller placed subcutaneously. The surgeon implants 306 the chemosensor with its sensor element in the striatum. The surgeon also implants 308 a stimulus electrode such that its exposed electrode surface is in or directly adjacent to the STN of the subject. Some or all of the openings in the subject's skull may then be closed.

In an embodiment for use in subjects having symptoms only on one side, the electrode and chemosensor are implanted on only the affected side of the subject's brain; while in an alternative embodiment for use in subjects having symptoms on both sides of their bodies, an electrode 206 is implanted in each STN and a sensor 204 is implanted in each striatum such that a pair are implanted on each side the subject's brain.

Figure 7:
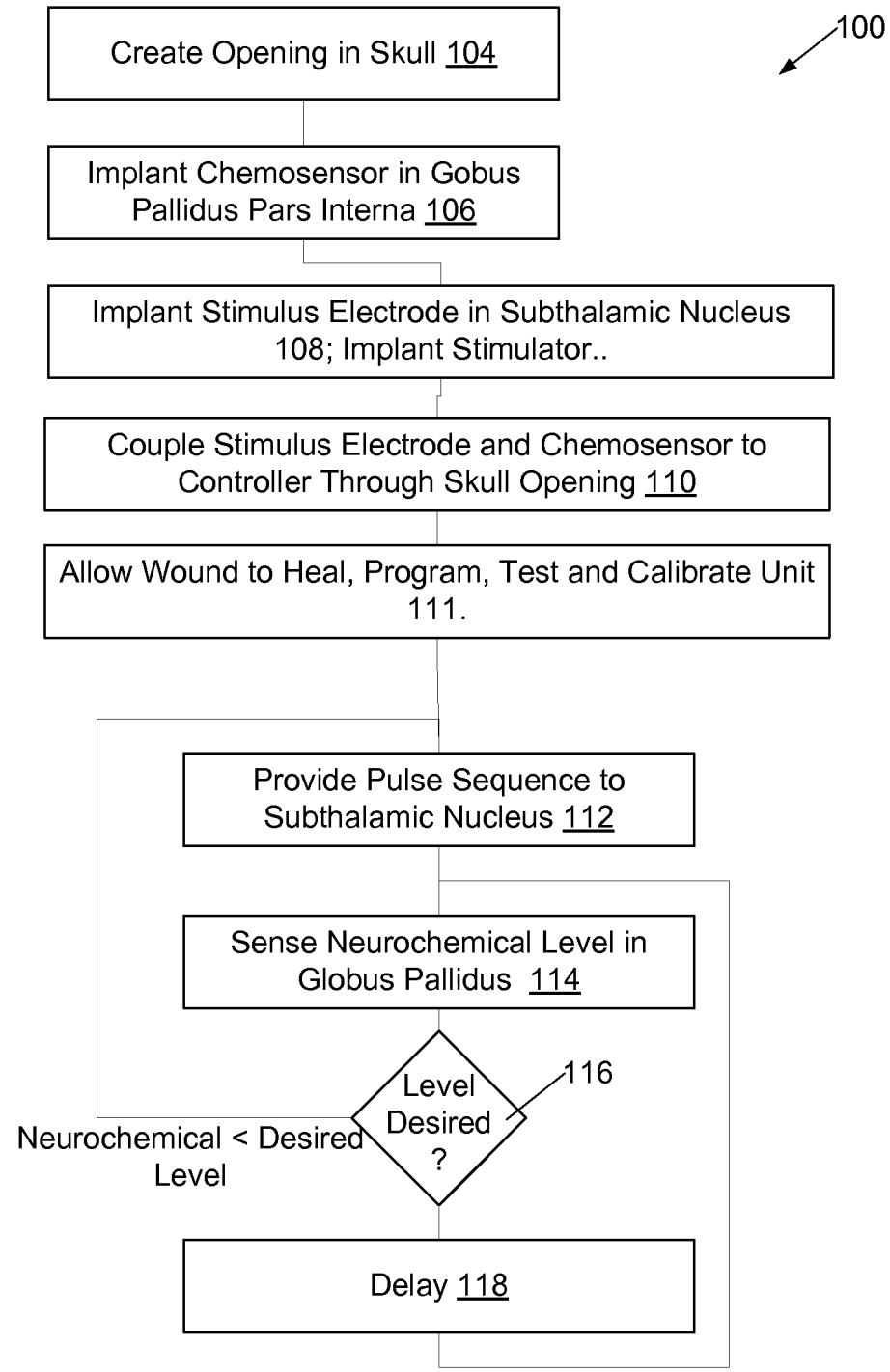
FIG. 7 is a flowchart illustration of the method of using the present device for treating Parkinson's Disease (PD).

The surgeon passes wires connected to each chemosensor and stimulus electrode through an opening in the subject's skull and couples 310 the wires to a control unit resembling that used in the embodiment of FIG. 7.

The stimulator control unit then executes a sequence where the control unit provides stimulus pulses 312 through electrode into the STN for a period of time sufficient to keep the targeted neurotransmitter levels near a specified level, in an embodiment within ten percent of the target level. The specified target level will be in the range of from ten to two hundred micromolar and will be prescribed by a physician based on the severity of the disease and the other therapies each patient receives, and may follow a diurnal pattern coordinated with a patient's anticipated activities to provide good control when the subject patient is performing fine motor activities while allowing recovery of stimulated tissue when the subject is inactive. Stimulation may be continuous or intermittent; following patterns as previously discussed with reference to the embodiment of FIG. 7. The control unit is programmable as previously discussed to allow adjustment of the stimulus prescription to best control symptoms in the subject or patient.

The control unit then reads chemosensor output to sense 314 dopamine levels in the striatum. If the sensed neurochemical level is less than a predetermined desired level 316, the control unit automatically repeats stimulus pulses 312 through the electrode implanted in the STN on the same side of the subject's brain as the chemosensor. If the sensed neurochemical level is greater than the predetermined desired level the control unit waits 318 and repeats sensing of the neurochemical level. Since the neurochemical level must drop below the threshold before stimulation is resumed, and the delay is shorter than the time constants of the neurochemical levels in tissue, the net effect is to control the stimulus to maintain the dopamine level in the striatum near the desired level.

Stimulator for Treatment of Benign Essential Tremor

In yet another embodiment, intended for control of the symptoms of Benign Essential Tremor (BET), stimulation is performed in the thalamus, and feedback is taken from a chemosensor in the striatum.

Figure 8:
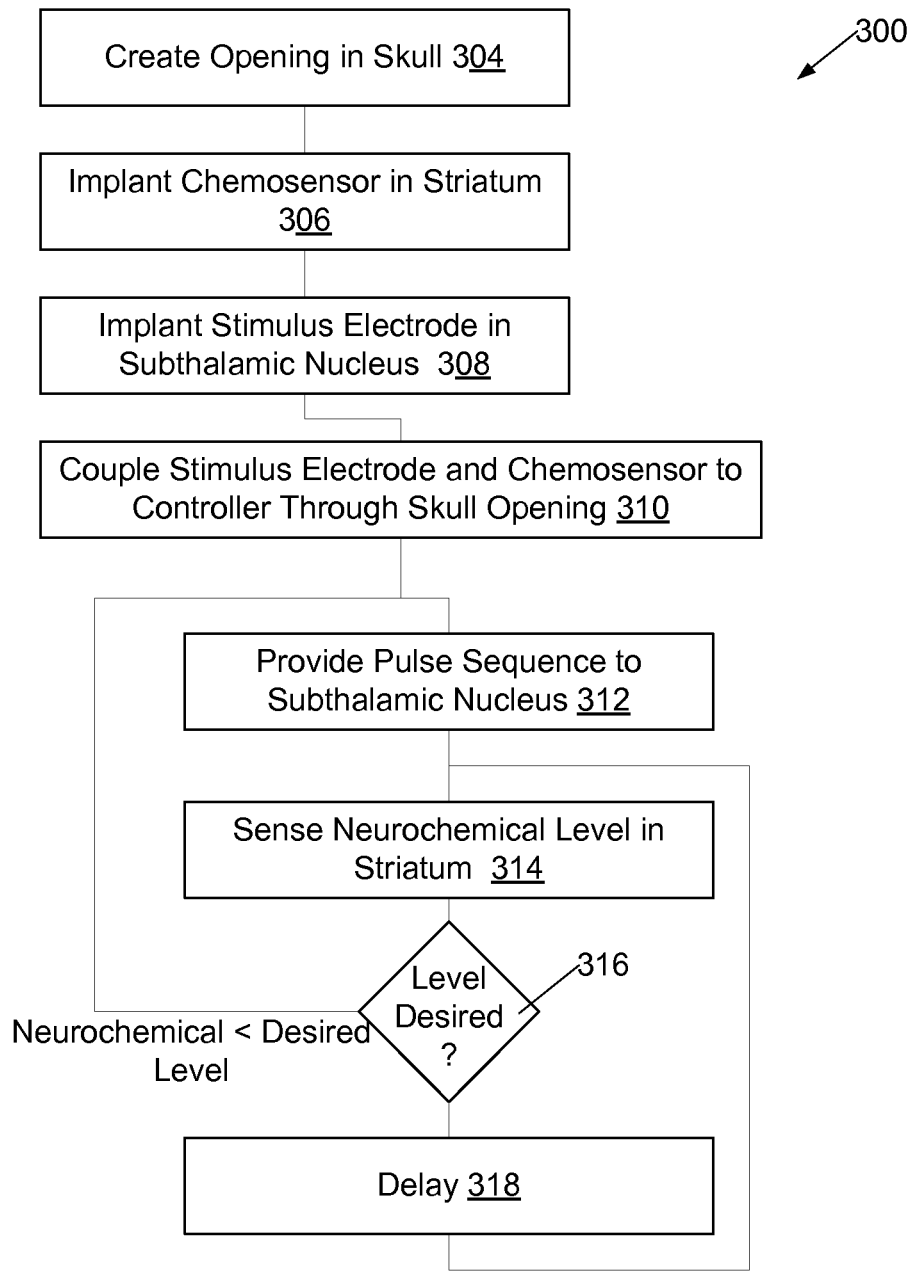
FIG. 8 is a flowchart illustration of an alternative method of using the present device for treating Parkinson's Disease (PD).

In this embodiment, a stimulus electrode is placed in the thalamus, and a dopamine chemosensor is placed in the striatum, in a manner similar to that previously discussed with reference to the embodiment of FIG. 8.

Stimulus pulse widths, patterns, pulse rates, pulse currents, and pulse voltages are similar to those previously discussed with reference to the embodiments of FIGS. 7 and 8. The feedback loop, whereby the neurostimulation performed depends inversely with the amount of the sensed neurochemical (dopamine) detected in the striatum, is essentially similar to that of the embodiments of FIGS. 7 and 8.

Feedback Stimulator for Other Conditions

It is believed that chemosensors for such neurochemicals as acetylcholine, norepinephrine, epinephrine, serotonin, and the dopamine precursor L-DOPA and dopamine metabolite DOPAC can be prepared and should prove operable with the system, in addition to the dopamine and glutamate sensors previously discussed. It is expected that such a chemosensor may be used in an area other than the GPi, with a stimulus electrode in a brain area other than the STN, to treat certain other conditions such as depression and narcolepsy. When treating narcolepsy, programmability of the feedback control unit with a diurnal rhythm may be particularly helpful—for example the unit may be programmed to stop stimulus or decrease target neurochemical levels shortly before a subject's bedtime, while resuming stimulus or increasing target levels shortly before the subject's scheduled awakening.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A deep brain stimulator device comprising:
   an implantable chemosensor selected from the group consisting of a dopamine-sensitive chemosensor and a glutamate sensitive chemosensor;
   an implantable stimulus electrode for electrical stimulation to a brain;
   a programmable feedback controller coupled to the chemosensor and the implantable stimulus electrode;
   wherein the feedback controller reads the chemosensor and provides a sequence of high frequency electrical stimulation (HFS) pulses through the stimulus electrode such that a greater number of HFS pulses are provided when levels of a neurochemical measured with the chemosensor are less than a programmed level than a number of HFS pulses provided when levels of the neurochemical measured with the chemosensor are greater than the programmed level;

wherein the chemosensor and the stimulus electrode are adapted for implantation in separate neurological structures of the brain;

wherein the HFS comprises electrical pulses at a rate of between one hundred and one hundred eighty pulses per second and of width between ten and twenty-five microseconds; and wherein the HFS pulses have a selected pulse parameter selected from the group consisting of voltage or current, and wherein an amplitude of the selected pulse parameter is inversely proportional to the neurochemical level as measured by the chemosensor.

2. The deep brain stimulator device of claim 1, wherein the HFS pulses are provided in bursts, and the bursts are burst-length-modulated in response to chemosensor readings of levels of the neurochemical.

3. The deep brain stimulator device of claim 1, wherein the feedback controller is programmable through signals electromagnetically coupled through skin to determine a pulse parameter for use when the chemosensor indicates the neurochemical level is low and the pulse parameter for use when the chemosensor indicates the neurochemical level is high; and wherein HFS pulses are provided in bursts, and the bursts are burst-length-modulated in response to chemosensor readings such that fewer pulses are provided when the chemosensor indicates that the neurochemical level is high.

4. The deep brain stimulator device of claim 1, wherein the feedback controller is configurable to provide HFS pulses through a determined first pair of electrodes in a multiple-electrode assembly when the neurochemical level is low and a determined second pair of electrodes when the neurochemical level is high.

5. The deep brain stimulator device of claim 4, wherein the feedback controller is programmable through signals electromagnetically coupled through skin to determine which of the first and second pairs of electrodes is used when the neurochemical level is low.

6. The deep brain stimulator device of claim 1, wherein the feedback controller is programmable through signals electromagnetically coupled through skin to follow a diurnal rhythm.

* * * * *